(12) United States Patent
Profio et al.

(10) Patent No.: US 9,642,589 B2
(45) Date of Patent: May 9, 2017

(54) SYSTEMS AND METHODS FOR GUIDED SELECTION OF ACQUISITION PARAMETERS FOR MEDICAL IMAGING

(71) Applicant: General Electric Company, Schenectady, NY (US)

(72) Inventors: Mark Vincent Profio, Waukesha, WI (US); Darin Robert Okerlund, Waukesha, WI (US); Scott D. Slavic, Sussex, WI (US); Bradley Jay Gabrielse, Waukesha, WI (US); Priti Madhav, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/755,597

(22) Filed: Jun. 30, 2015

(65) Prior Publication Data

US 2017/0000447 A1     Jan. 5, 2017

(51) Int. Cl.
*A61B 6/00*       (2006.01)
*A61B 6/03*       (2006.01)

(52) U.S. Cl.
CPC .............. *A61B 6/545* (2013.01); *A61B 6/032* (2013.01); *A61B 6/461* (2013.01)

(58) Field of Classification Search
USPC ................................................... 378/1, 4, 8
See application file for complete search history.

(56) References Cited

U.S. PATENT DOCUMENTS

| | | |
|---|---|---|
| 7,006,862 B2 | 2/2006 | Kaufman et al. |
| 7,613,672 B2 | 11/2009 | West et al. |
| 7,668,286 B2 | 2/2010 | Tsuyuki et al. |
| 7,979,378 B2 | 7/2011 | West et al. |
| 8,175,356 B2 | 5/2012 | Movassaghi et al. |
| 2003/0092983 A1 | 5/2003 | Baker et al. |
| 2004/0131141 A1 | 7/2004 | Horiuchi |
| 2010/0014628 A1 | 1/2010 | Kadomura et al. |
| 2011/0268335 A1 | 11/2011 | Kunze et al. |
| 2012/0014499 A1 | 1/2012 | Feuerlein et al. |
| 2014/0192952 A1 | 7/2014 | Keall et al. |

OTHER PUBLICATIONS

International Search Report and Written Opinion for corresponding PCT application PCT/US2016/031718, dated Aug. 29, 2016; 5 pages.

*Primary Examiner* — Nicole Ippolito
*Assistant Examiner* — Hanway Chang
(74) *Attorney, Agent, or Firm* — Dean D. Small; The Small Patent Law Group, LLC.

(57) ABSTRACT

Systems and methods are provided that receive a clinical identifier, an acquisition condition target, and one or more patient characteristics. The systems and methods further generate a scan attribute based on the clinical identifier. The scan attribute corresponding to characteristics of a resultant medical image. The systems and methods determine select scan settings from a plurality of scan settings based on the scan attribute and the one or more patient characteristics, and calculate candidate acquisition conditions associated with the select scan settings. Further, the systems and methods identify one of the select scan settings as a scan prescription based on a relation between the candidate acquisition conditions and the acquisition condition target.

20 Claims, 6 Drawing Sheets

FIG. 4

SYSTEMS AND METHODS FOR GUIDED SELECTION OF ACQUISITION PARAMETERS FOR MEDICAL IMAGING

BACKGROUND OF THE INVENTION

The subject matter disclosed herein relates generally to systems and methods for computed tomography (CT) imaging.

In CT imaging, an X-ray source may be rotated around an object of interest (e.g., a patient, organ of a patient) to obtain imaging information. The object of interest is injected with a contrast agent (e.g., radiocontrast agent, an ionic contrast agent, a barium sulfate contrast agent, a blood agent) to provide maximum contrast in the imaging information. During a scan, X-rays emitted from the X-ray source, attenuated by the object of interest, may be collected or detected by a detector and used to reconstruct a medical image. Optionally, the CT imaging may include dual-energy (DE) CT imaging by having the X-rays emitted from the X-ray source switch between two energy level ranges.

Acquisition settings correspond to a plurality of user selections defining various mechanical and/or processing actions to acquire and/or reconstruct the imaging information. The acquisition settings form a scan prescription effecting characteristics of the medical image such as coverage size, spatial resolution, and/or the like. The acquisition settings are interdependent with one another, requiring the user to adjust numerous acquisition settings to adjust a characteristic of the medical image. Due to the interdependencies, users anecdotally develop groupings of acquisition settings focused on providing machine specific adjustments. However, the developed groups do not account for variations in patient anatomies, which result in the user manually adjusting the acquisition settings corresponding to trade-offs in dose and image quality. Thus, there is a need for ensuring reliable diagnostic outcomes with consistent image quality of medical images, across patients, using CT imaging.

BRIEF DESCRIPTION OF THE INVENTION

In one embodiment, a method is provided that may include receiving a clinical identifier, an acquisition condition target, and one or more patient characteristics. The method may also include generating a scan attribute based on the clinical identifier. The scan attribute corresponding to characteristics of a resultant medical image. The method may also include determining select scan settings from a plurality of scan settings based on the scan attribute and the one or more patient characteristics, and calculating candidate acquisition conditions associated with the select scan settings. Further, the method may include identifying one of the select scan settings as a scan prescription based on a relation between the candidate acquisition conditions and the acquisition condition target.

In another embodiment, an imaging system is provided. The imaging system may include an acquisition unit that includes a computed tomography (CT) detector configured to collect imaging data based on a scan prescription. The imaging system may also include a processing unit having one or more processors. The processing unit is operably coupled to the acquisition unit. The processing unit may be configured to receive a clinical identifier, an acquisition condition target, and one or more patient characteristics. The processing unit may also be configured to generate a scan attribute based on the clinical identifier. The scan attribute corresponds to characteristics of a resultant medical image. The processing unit may also be configured to determine select scan settings from the plurality of scan settings based on the scan attribute and the one or more patient characteristics. Further, the processing unit may be configured to calculate candidate acquisition conditions associated with the select scan settings, and identify one of the select scan setting as a scan prescription based on a relation between the candidate acquisition conditions and the acquisition condition target.

In another embodiment, a tangible and non-transitory computer readable medium is provided. The tangible and non-transitory computer readable medium includes one or more computer software modules configured to direct one or more processors. The tangible and non-transitory computer readable medium may direct the one or more processors to receive a clinical identifier, an acquisition condition target, and one or more patient characteristics. The tangible and non-transitory computer readable medium may also direct the one or more processors to generate a scan attribute based on the clinical identifier. The scan attribute corresponds to characteristics of a resultant medical image. The tangible and non-transitory computer readable medium may also direct the one or more processors to determine select scan settings from the plurality of scan settings base on the scan attribute and the one or more patient characteristics. Further, the tangible and non-transitory computer readable medium may also direct the one or more processors to calculate candidate acquisition conditions associated with the select scan settings, and identify one of the select scan settings as a scan prescription based on a relation between the candidate acquisition conditions and the acquisition condition target.

BRIEF DESCRIPTION OF THE DRAWINGS

FIG. 4 illustrates a display interface shown on a display in accordance with various embodiments.

DETAILED DESCRIPTION OF THE INVENTION

Figure 1:
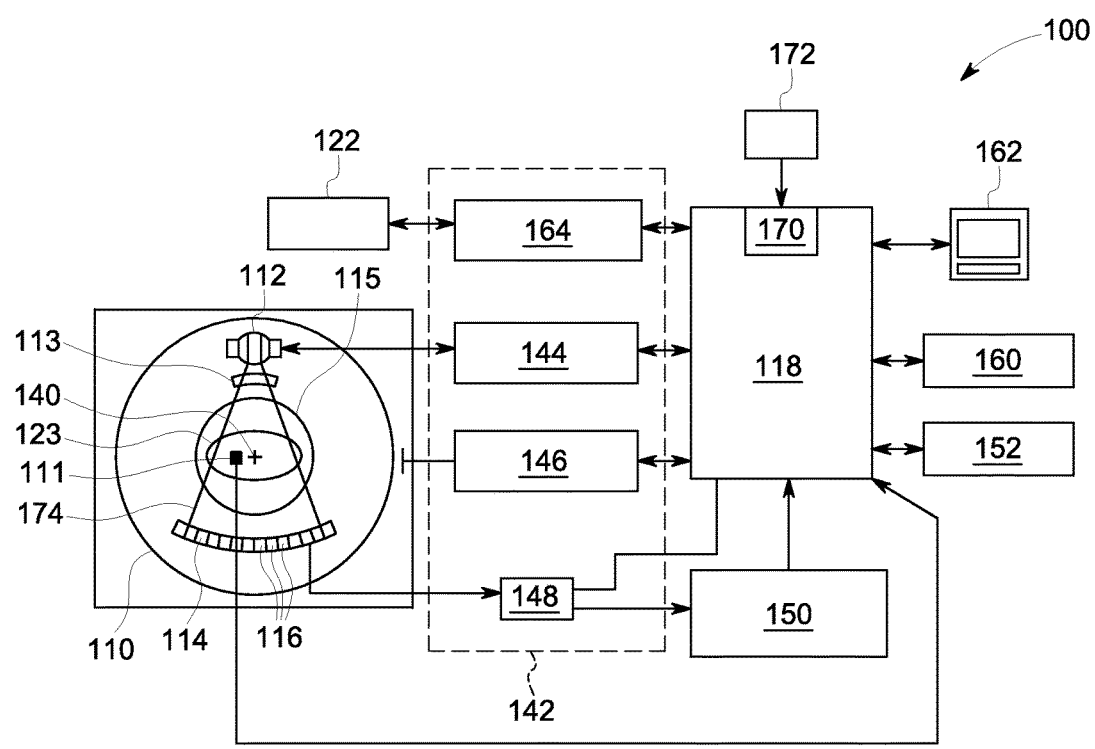
FIG. 1 is a schematic block diagram illustrating an imaging system in accordance with various embodiments described herein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for providing guidance on selection of acquisition or scan parameters for medical imaging, such as for, computed tomography (CT) imaging and/or dual energy CT (DECT) imaging. The selection of acquisition parameters are based on a clinical identifier (CID), patient attributes or characteristics (e.g., size, attenuation, age, heart rate), and an acquisition condition target (e.g., contrast dosage target, noise index). The CID provides a clinical context having multiple candidate acquisition settings. The CID may include an anatomy of interest and a clinical scan identification. The CID is logically mapped to a profile database for selection of clinically relevant prioritization of primary scan or "critical to quality" attributes corresponding to one or more characteristics of the resultant medical image. The scan attributes may include a temporal resolution, a material discrimination accuracy, a contrast to noise ratio, a coverage size, a spatial resolution, an artifact suppression attribute, and/or the like. The profile database provides a viable set of candidate acquisition or scan settings having variable scan field of views, collimation widths, gantry rotation speeds, focal spot sizes, and/or the like. Based on the CID, the patient attributes, and acquisition condition target, the systems and methods provided herein automatically identify select (e.g., optimal) acquisition settings or a scan prescription from the candidate acquisition settings from the profile database.

Additionally or alternatively, the profile database may include corresponding reconstruction settings associated with the candidate acquisition settings or scan settings, which may be used to generate secondary or additional reconstruction images. The reconstruction settings may include select keV energy level(s), iterative reconstruction (e.g., adaptive statistical reconstruction), direct multi-planar reconstruction, algorithmic reconstruction (e.g., Native VUE®), and/or the like. Optionally, an image based CID may be specified and attached to one or more of the reconstructed medical images. For example, the image based CID may be used as a flag indicating pre-determined diagnostic and/or measurements to be performed.

A technical effect of various embodiments described herein include automated guidance for the clinical use case (e.g., based on the CID) on the varied and complex trade-offs necessary to ensure reliable diagnostic outcomes with consistent image quality across patients. A technical effect of various embodiments described herein include a patient specific selection of acquisition or scan settings to define a scan prescription more efficiently, while improving quality assurance and managing an X-ray radiation dose of the patient. A technical effect of various embodiments described herein include repeatable CT scanning examinations with fewer scan time decisions (e.g., reduced opportunities for user error, increased user experience) with a simple and consistent workflow across all modes of CT operation.

FIG. 1 illustrates a schematic diagram of an exemplary CT imaging system 100 that may be utilized to implement various embodiment discussed herein. Although the CT imaging system 100 is illustrated as a standalone imaging system, it should be noted that the CT imaging system 100 may form part of a multi-modality imaging system in some embodiments. For example, the multi-modality imaging system may include the CT imaging system 100 and a positron emission tomography (PET) imaging system, or a single photon emission computed tomography (SPECT) imaging system. It should also be understood that other imaging systems capable of performing the functions described herein are contemplated as being used.

The CT imaging system 100 includes a gantry 110 that has the X-ray source 112 that projects a beam of X-rays toward the detector array 114 on the opposite side of the gantry 110. A source collimator 113 and a bowtie filter module (not shown) are provided proximate the X-ray source 112. The detector array 114 includes a plurality of detector elements 116 that are arranged in rows and channels that together sense the projected X-rays that pass through a patient 123 (e.g., object of interest). The imaging system 100 may include a physiologic sensor 111 (e.g., electrocardiogram (ECG), a respiratory sensor) proximate to the patient 123 for cardiac or respiratory gating.

A motorized table 122 is utilized to move the patient 123 into and out of the gantry 110. Particularly, the table 122 moves at least a portion of the patient 123 through a gantry opening 115 that extends through the gantry 110. Further, the table 122 may be used to move the patient 123 vertically within the bore of the gantry 110.

The depicted detector array 114 includes a plurality of detector elements 116. Each detector element 116 produces an electrical signal, or output, that represents the intensity of an impinging X-ray beam and hence allows estimation of the attenuation of the beam as it passes through the patient 123. During a scan to acquire the X-ray projection data, the gantry 110 and the components mounted thereon rotate about a center of rotation 140. FIG. 1 shows only a single row of detector elements 116 (i.e., a detector row). However, the multi-slice detector array 114 includes a plurality of parallel detector rows of detector elements 116 such that projection data corresponding to a plurality of slices can be acquired simultaneously during a scan.

In the exemplary embodiment, the X-ray source 112 and the detector array 114 are rotated with the gantry 110 within the imaging plane and around the patient 123 to be imaged such that the angle at which an X-ray beam 174 intersects the patient 123 constantly changes. A group of X-ray attenuation measurements, i.e., projection data, from the detector array 114 at one gantry angle is referred to as a "view" or "projection." A "scan" of the patient 123 comprises a set of views made at different gantry angles, or view angles, during one or more revolutions of the X-ray source 112 and the detector array 114. In a CT scan, the projection data is processed to reconstruct an image that corresponds to a three-dimensional volume taken of the patient 123. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Rotation of the gantry 110, the operation of the X-ray source 112, and position of the motorized table 122 are governed by an acquisition subsystem 142 based on one or more scan settings (e.g., tube current/voltage, focal spot size, duty cycle, kV pair, rotation speed, collimation width, field of view size, body dose, exposure time, head dose, helical pitch) defined by a scan prescription. The acquisition subsystem 142 includes an X-ray controller 144 that provides power and timing signals to the X-ray source 112 based on the scan settings defined by the scan prescription. The X-ray controller 144 may deliver power (e.g., tube current, tube voltage) and/or configure the X-ray source 112 to project X-rays having a certain field of view and/or collimation width (e.g., collimation slab) based on the scan settings defined by the scan prescription. Additionally or alternatively, the X-ray controller 144 may control a focal spot size of the X-ray source 112 based on the scan settings defined by the scan prescription. Optionally, for dual-energy CT scans, the X-ray controller 144 may define the dual energy levels (e.g., kV pair) and duty cycle of the X-rays emitted by the X-ray source 112.

The acquisition subsystem 142 also includes a gantry motor controller 146 that controls the rotational speed and position of the gantry 110. For example, the gantry motor controller 146 may rotate the gantry 110 at a rotational velocity based on the scan settings defined by the scan prescription.

In addition, the acquisition subsystem 142 may also include a table motor controller 164 that controls the motorized table 122 to position the patient 123 in the gantry 110 based on the scan settings defined by the scan prescription. Particularly, the motorized table 122 moves at least a portion of the patient 123 through the gantry opening.

The scan prescription may be stored on a storage device 152, which is communicatively coupled to the acquisition subsystem 142. The storage device 152 may be a tangible and non-transitory computer readable medium such as flash memory, RAM, ROM, EEPROM, and/or the like. The scan prescription may be defined by a processing unit 118.

The processing unit 118 may include one or more processors that execute software or firmware stored in memory (e.g., the storage device 152) to perform the operations described herein. Optionally, the processing unit 118 may include a central controller circuit (CPU), one or more microprocessors, a graphics controller circuit (GPU), or any other electronic component capable of processing inputted data according to specific logical instructions. The processing unit 118 executes instructions stored on a tangible and non-transitory computer readable medium (e.g., the storage device 152, integrated memory of the processing unit 118) to perform various operations described herein. The processing unit 118 receives the projection data from the detector array 114 and processes the projection data to reconstruct an image of the patient 123.

Additionally or alternatively, the processing unit 118 may be configured to identify one or more acquisition or scan settings from a profile database, which is used to define the scan prescription. The profile database may be a collection of candidate scan settings with associated scan attributes stored on the storage device 152. Additionally or alternatively, the profile database may be stored remotely, for example, on a remote server communicatively coupled (e.g., Ethernet, wireless, internet, networked) with the CT imaging system 100. The profile database may be generated from priori information (e.g., patient population acquisition studies, pre-programmed rule sets) and/or generated from user inputs from a user interface 160. The profile database may be used as look up table by the processing unit 118 to match a corresponding scan attribute with corresponding scan settings.

The scan attributes may correspond to a characteristic, such as an image characteristic, of a medical image(s) that is reconstructed by the processing unit 118 based on the corresponding scan settings. For example, the scan attribute may be a temporal resolution, a material discrimination accuracy (MDA), a contrast to noise ratio, a coverage size, a spatial resolution, a low contrast detectability, minimal coverage time, an artifact suppression attribute, and/or the like.

The processing unit 118 is operably coupled to a display 162 and the user interface 160. The display 162 may include one or more liquid crystal displays (e.g., light emitting diode (LED) backlight), organic light emitting diode (OLED) displays, plasma displays, CRT displays, and/or the like. The display 162 allows the operator to observe the reconstructed image and other data generated by the processing unit 118. For example, the display 162 may display patient information, one or more CT images, components of a display interface, measurements, diagnosis, treatment information, and/or the like.

The user interface 160 controls operations of the CT imaging system 100 and is configured to receive inputs (e.g., CID) from the user. The user interface 160 may include a keyboard, a mouse, a touchpad, one or more physical buttons, and/or the like. Optionally, the display 162 may be a touch screen display, which includes at least a portion of the user interface 142. For example, the user may select one or more user selectable elements shown on the display by touching or making contact with touch sensitive portions of the display 162.

A data acquisition system (DAS) 148 in the acquisition subsystem 142 samples analog data from detector elements 116 and converts the data to digital signals for subsequent processing. An image reconstructor 150 receives the sampled and digitized X-ray data from the DAS 148 and performs high-speed image reconstruction. The image reconstructor 150 may generate the resultant medical image based on reconstructed settings received via the user interface 162 and/or based on the scan attributes. The reconstruction settings may include select keV energy level(s), iterative reconstruction (e.g., adaptive statistical reconstruction), direct multi-planar reconstruction, algorithmic reconstruction (e.g., Native VUE®), and/or the like. The reconstructed medical images are input to the processing unit 118 that stores the image in a storage device 152.

Optionally, an image based CID may be specified and attached to one or more of the reconstructed medical images by the image reconstructor 150 and/or the processing unit 118. For example, the image based CID may be used as a flag indicating pre-determined diagnostic and/or measurements to be performed.

Additionally or alternatively, the processing unit 118 includes a device 170, for example, a CD-ROM drive, DVD drive, magnetic optical disk (MOD) device, or any other digital device including a network connecting device such as an Ethernet device for reading instructions and/or data from a tangible non-transitory computer-readable medium 172, that excludes signals, such as a CD-ROM, a DVD or another digital source such as a network or the Internet, as well as yet to be developed digital means.

Figure 2:
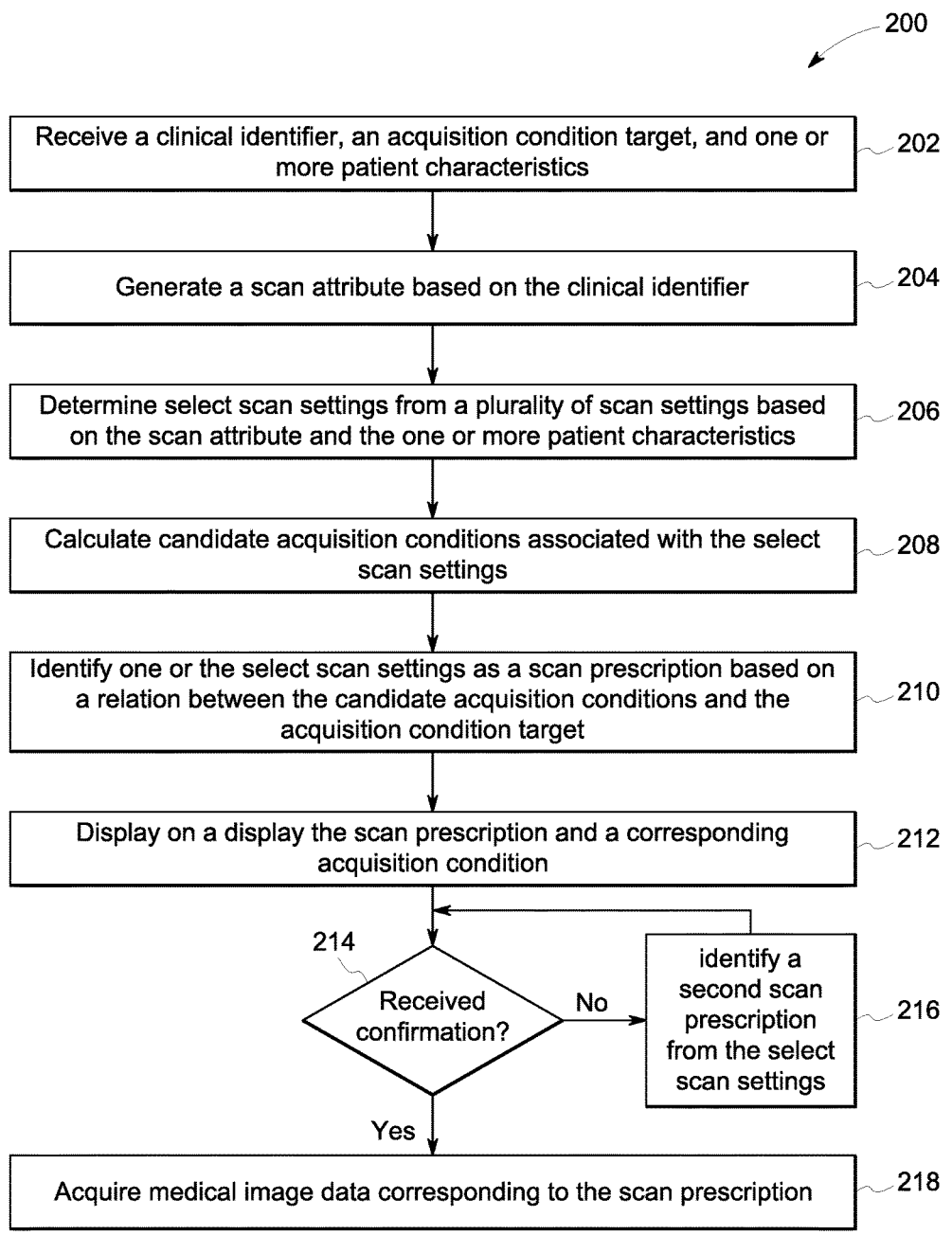
FIG. 2 is a flowchart of a method in accordance with various embodiments.

FIG. 2 illustrates a flowchart of a method 200 for guided selection of acquisition settings for imaging systems. The method 200, for example, may employ structures or aspects of various embodiments (e.g., systems and/or methods) discussed herein, such as the CT imaging system 100. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein. It should be noted, other methods may be used, in accordance with embodiments herein. All or a portion of the operations of FIG. 2 are performed by one or more processors executing software or firmware stored in memory of the system 100.

One or more methods may (i) receive a clinical identifier, an acquisition condition target, and one or more patient characteristics; (ii) generate a scan attribute based on the clinical identifier; (iii) determine select scan settings from a plurality of scan settings based on the scan attribute and the one or more patient characteristics; (iv) calculate candidate acquisition conditions associated with the select scan settings; and (v) identify one of the select scan settings as a scan prescription based on a relation between the candidate acquisition conditions and the acquisition condition target.

Beginning at 202, a clinical identifier (CID), an acquisition condition target, and one or more patient characteristics are received by the processing unit 118. The CID corresponds to a clinical context for the scan. For example, the CID may include an anatomy of interest (e.g., organ of interest, region of interest) of the patient 123 and a clinical indication. The clinical indication may correspond to the purpose or objective of the CT scan. For example, the clinical indication may correspond to a lesion on the anatomy of interest, a follow-up CT scan after a medical procedure, an imbedded medical device approximate to the anatomy of interest (e.g., stent), and/or the like.

The CID may be received by the processing unit 118 from the user interface 160. For example, the CID may be selected by the user from a plurality of candidate CIDs displayed on a display interface (e.g., the display interface 300 shown in FIG. 3) or graphical user interface (GUI) shown on the display 162. The GUI may include one or more interface components (e.g., a corresponding to user selectable elements shown visually on the display 162, and may be selected, manipulated, and/or activated by the user operating the user interface 160 (e.g., touch screen, keyboard, mouse). The interface components may be presented in varying shapes and colors, such as a graphical or selectable icon, slide bar, and/or the like. Optionally, one or more interface components may include text or symbols, such as a drop-down menu, a menu bar, a title bar, a window (e.g., a pop-up window) and/or the like. Additionally or alternatively, one or more interface components may indicate areas within the GUI for entering or editing information (e.g., CID, patient characteristics) within the GUI, such as a text box, a text field, and/or the like.

The acquisition condition target may be received by the processing unit 118 from the user interface 160. For example, by the user selecting or entering the acquisition condition target using one or more interface components of the GUI shown on the display 162. The acquisition condition target may correspond to an image quality target and/or a dose or dosage target of the patient. The image quality target may be a noise index of the reconstructed medical image generated by the processing unit 118. The noise index may be a desired standard deviation of noise (e.g., statistical variations in the X-ray data) between pixels of the resultant medical image (e.g., the one or more reconstructed images generated by the processing unit 118). The noise index may be a scaled value from zero to one hundred selected by the user using the user interface 160 representing an amount of noise of the resultant medical image. For example, a noise index proximate to zero will have less noise relative to a noise index proximate to one hundred. The dose or dosage target may represent a target amount of energy (e.g., X-ray radiation) deposited within a tissue of the patient 123 in relation to a mass of the patient 123 during the CT scan.

The one or more patient characteristics may corresponds to physiological features of the patient. For example, the age of the patient 123, weight of the patient 123, height of the patient 123, a calculated body mass index of the patient 123, patient diameter, position of the patient relative to the gantry 110, and/or the like. The one or more patient characteristics may be received by the processing unit 118 from the user interface 160. Additionally or alternatively, a size and/or position of the patient 123 may be determined by the processing unit 118 based on a scout image or photo/video captured of the patient 123.

Optionally, the one or more patient characteristics may be measured by the processing unit 118 from a scout or preliminary scan performed by the CT imaging system 100. For example, the one or more patient characteristics may include an attenuation of the patient 123 determined from the scout scan. Additionally or alternatively, the one or more patient characteristics may be based on the CID. For example, the age of the patient 123, organ function (e.g., organ infection, disease), known diseases, patient history, gender, max breathold, and/or the like may be derived from the anatomy of interest of the patient 123 and/or the clinical indication.

Generally at 204 and 206, the processing unit 118 may logically map the CID to select scan settings from the profile database.

At 204, a scan attribute based on the CID is generated by the processing unit 118. The scan attribute corresponds to a characteristic(s), such as an image characteristic, of the resultant medical image reconstructed by the processing unit 118. For example, the scan attribute may be a temporal resolution, a material discrimination accuracy (MDA), a contrast to noise ratio, a coverage size, a spatial resolution, an artifact suppression attribute, a low contrast detectability (LCD), a minimal coverage time, and/or the like. Optionally, the scan attribute may include a primary scan attribute corresponding to a select or priority characteristic that is used during diagnostics or measurements in relation to the CID. For example, the CID corresponds to a kidney stone characterization. The primary scan attribute for the kidney stone characterization may be a high material discrimination accuracy (MDA) to determine the components of the kidney stone. It should be noted that the CID may have more than one primary scan attribute. For example, the CID corresponds to an abdominal CT angiography. The primary scan attributes for the abdominal CT angiography may be a high contrast and coverage size.

The processing unit 118 may determine the scan attributes (e.g., primary scan attributes, secondary scan attributes, degree of freedom attributes) for the corresponding CID based on a scan attribute table. The scan attribute table may be a collection of candidate scan attributes with associated CIDs. The scan attribute table may be stored on the storage device 152. Additionally or alternatively, the scan attribute table may be stored remotely, for example, on a remote server communicatively coupled (e.g., Ethernet, wireless, internet, networked) with the CT imaging system 100. The scan attribute table may be used as a look up table by the processing unit 118 to match a corresponding CID received by the processing unit 118 with a corresponding scan attribute. The scan attribute table may be generated from user inputs from the user interface 160. Optionally, the scan attribute table may be generated from priori information (pre-programmed rule sets).

Optionally, the scan attribute table may include secondary scan attributes and degree of freedom attributes. The secondary scan attributes may include data of interest for the user but may correspond to a characteristic(s) of the resultant medical image that is not primarily used or necessary for diagnostics or measurements, relative to the primary scan attribute, based on the CID. For example, the scan attribute table may have the CID corresponding to the abdominal CT angiography include secondary scan attributes of both high spatial and temporal resolution.

The degree of freedom attributes may correspond to characteristic(s) of the resultant medical image that is not needed for the diagnostics or measurements based on the CID. The degree of freedom attributes may be characteristics that are optional, may be omitted, and/or may have minimal value relative to the primary and/or secondary scan attribute. For example, the scan attribute table may have the CID corresponding to the abdominal CT angiography include degree of freedom attributes of MDA.

At 206, select scan settings from a plurality of scan settings are determined based on the scan attribute and the one or more patient characteristics by the processing unit 118. The processing unit 118 may select one or more of the select scan settings from the profile database. For example, the processing unit 118 may compare the scan attributes of the profile database with the scan attributes generated at 204. When the processing unit 118 determines a match, the processing unit 118 may flag the corresponding scan settings.

The processing unit 118 may select from the flagged scan settings based on the one or more patient characteristics. For example, one of the patient characteristics correspond to a high attenuation of the patient 123 measured from a scout scan. Based on the measured attenuation, the processing unit 118 may discard scan settings having high tube current. In another example, one of the patient characteristics corresponds to a small size of the patient. Based on the small size of the patient, the processing unit 118 may discard scan settings having large body field of views.

Optionally, the processing unit 118 may ignore and/or disregard a subset of the scan attributes, such as the degree of freedom attributes and/or a secondary attributes, if the processing unit 118 could not find a match of the primary scan attributes from the profile database. For example, the CID may correspond to an instrumented spine having primary scan attributes of a high spatial resolution and artifact suppression attribute, a secondary scan attribute of a low contrast detectability, and degree of freedom attributes of temporal resolution and MDA. The processing unit 118, based on the primary, secondary, and degree of freedom scan attributes of the CID, may determine that the profile database does not include a match for the scan attributes (e.g., the primary scan attributes) of the CID. When no match was found, the processing unit 118 may automatically ignore and/or disregard the degree of freedom attributes of the scan attributes of the CID to determine a match within the profile database. For example, the processing unit 118 may compare the scan attributes of the profile database with only the primary and secondary scan attributes of the CID. Optionally, the processing unit 118 may display a warning and/or alert window on the display 162 to request confirmation and/or to inform the user that the select scan settings may not result in one or more scan attributes of the CID.

If a match is still not found by the processing unit 118 when the degree of freedom attributes were ignored, the processing unit 118 may additionally ignore and/or disregard the secondary scan attribute of the CID to determine a match within the profile database. For example, the processing unit 118 may compare the scan attributes of the profile database with only the primary scan attributes of the CID.

At 208, candidate acquisition conditions associated with the select scan settings are calculated by the processing unit 118. The processing unit 118 may calculate the candidate acquisition conditions for the select scan settings. For example, the acquisition condition may correspond to a projected image quality of the resultant medical image, such as a projected noise index. The processing unit 118 may calculate projected noise indexes, which may correspond to the candidate acquisition conditions, from the select scan settings selected at 206.

In another example, the candidate acquisition condition may correspond to a projected dosage (e.g., amount of absorbed X-ray radiation) of the patient 123 during the CT scan. The projected dosage may be calculated by the processing unit 118 from the select scan settings selected at 206 and the one or more patient characteristics (e.g., weight, age, sex, height). For example, the select scan settings may define a max exposure time having a field of view. The processing unit 118 may calculate the projected dosage or amount of energy (e.g., X-ray radiation) deposited within a tissue of the patient 123 based from the one or more patient characteristics (e.g., weight, age, sex, height) and the corresponding select scan settings. Additionally or alternatively, a projected dosage may be included within the profile database, which may be selected by the processing unit 118 when the select scan settings are identified.

At 210, one of the select scan settings is identified as a scan prescription based on a relation between the candidate acquisition conditions and the acquisition condition target. The processing unit 118 may select the select scan settings relating to a difference or disparity between the candidate acquisition conditions and the acquisition condition target by the processing unit 118. For example, the processing unit 118 may compare the candidate acquisition conditions with the acquisition condition target to determine which candidate acquisition candidate is most proximate with the acquisition condition target. The processing unit 118 may select one of the select scan settings having a corresponding candidate acquisition condition with the smallest different or disparity relative to the other candidate acquisition conditions of the remaining select scan settings as the scan prescription.

At 212, the scan prescription and a corresponding acquisition condition are displayed on the display 162 at the direction of the processing unit 118. Additionally or alternatively, more than one scan prescription (e.g., as described in connection at 216) with corresponding acquisition conditions may be displayed concurrently. In connection with FIG. 3, the scan prescription and the corresponding acquisition condition may be shown on the display 162 within a display interface 300.

Figure 3:
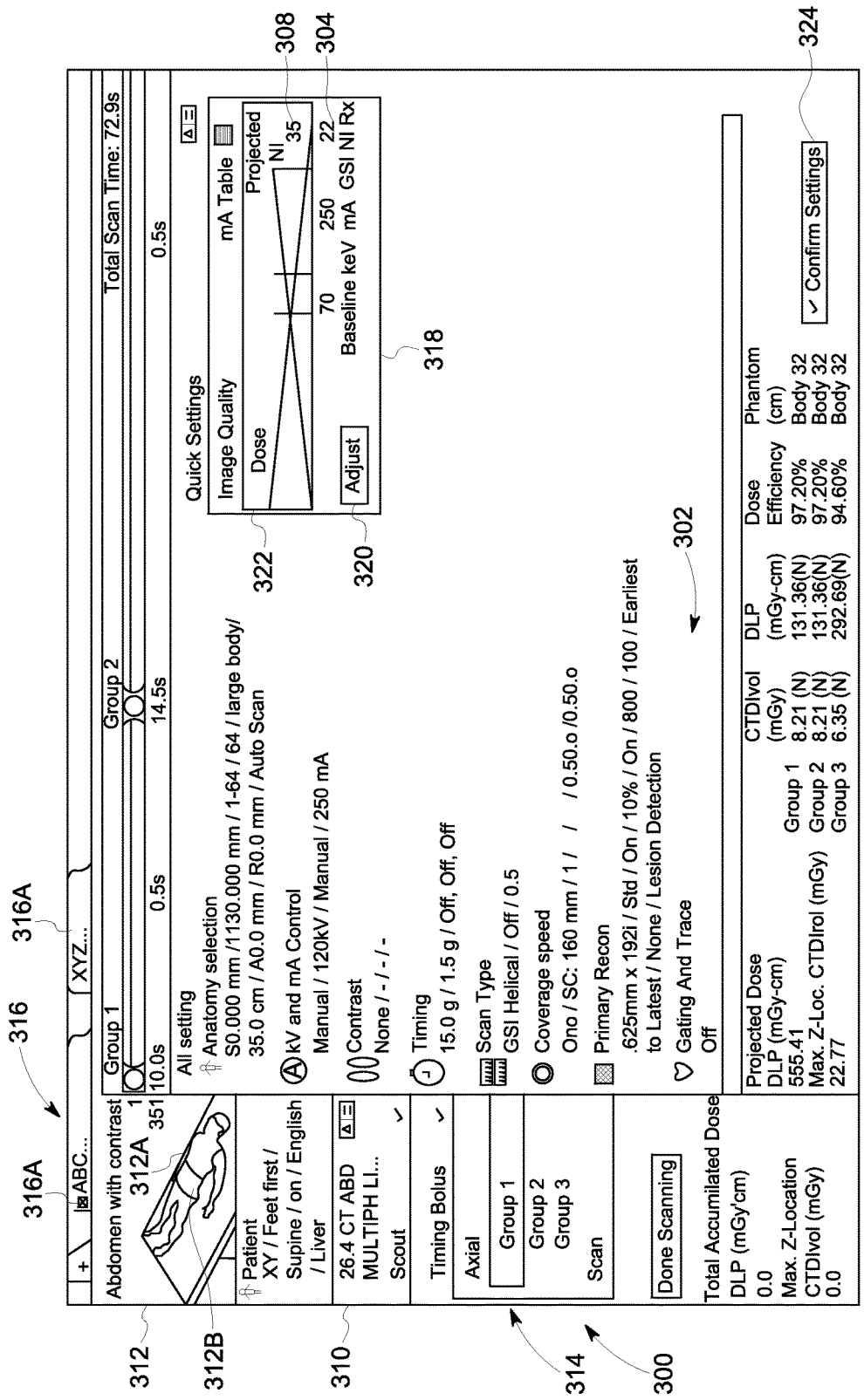
FIG. 3 illustrates a display interface shown on a display in accordance with various embodiments.

FIG. 3 illustrates the display interface 300 corresponding to a GUI shown on the display 162. The display interface 300 includes interface components corresponding to user selectable elements shown visually on the display 162, and may be selected, manipulated, and/or activated by the user operating the user interface 160 (e.g., touch screen, keyboard, mouse). The display interface 300 may be generated by the processing unit 118 using a display signal, which is received by the display 162.

The display signal may be a video interface (e.g., Video Graphics Array, DisplayPort, High Definition Multimedia Interface, Digital Visual Interface, MHL, SDI, and/or the like) used by the display 162. The display signal may correspond to a series of pixel configurations based on firmware or software stored on the storage device 152 and executed by the processing unit 118. The display signal may be used by the display 162 for displaying the display interface 300. For example, the display signal may be a series of packets along three channels corresponding to a red, green, and blue intensity value, respectively, of a pixel. The display 162 may adjust red, green, and blue intensity values of the pixels based on the received display signal.

The interface components may be presented in varying shapes and colors, such as a graphical or selectable window (e.g., acquisition condition window 318), slide bar, an icon 320, and/or the like. Optionally, one or more interface components may include text or symbols, such as a menu bar 314, a toolbar 316, a patient overview 312, drop-down menu 310, an activity window 302, and/or the like. Additionally or alternatively, one or more interface components may indicate areas within the GUI for entering or editing information (e.g., CID, patient characteristics) within the GUI, such as a text box, a text field, and/or the like.

The menu bar 314 and drop-down menu 310 may correspond to a list of textual or graphical user selectable elements from which the user may select. For example, the menu bar 314 may include one or more selectable operations or functions that may be performed by the processor unit 118 when selected by the user.

The toolbar 316 may correspond to an area of the display interface 300 that is subdivided into tabs or selectable icons 316*a* corresponding to select operation modes or patient configurations stored on the storage device 152. For example, the selectable icon 207*a* may correspond to a patient entry/access mode.

The patient overview 312 may correspond to a visual representation of the CID selected by the user. For example, the patient overview may include a pictorial representation 312*a* of the patient that includes a region of interest indicator 312*b* corresponding to a position of an anatomy of interest of the CID. Optionally, the patient overview 312 may include a textual content representing the CID and/or one or more patient characteristics.

The activity window 302 may correspond to an area of the display interface 300 for viewing the scan prescription and/or select scan settings selected by the processing unit 118. For example, the activity window 302 may include the acquisition parameters (e.g., tube current/voltage, focal spot size, duty cycle, kV pair, rotation speed, collimation width, field of view size, body dose, exposure time, head dose, helical pitch) corresponding to the select scan settings identified as the scan prescription at 210. Additionally or alternatively, the activity window 302 may include one or more medical images, measurements, diagnostic results, data entry (e.g., patient information), and/or the like.

The acquisition condition window 318 may include data corresponding to the candidate acquisition condition identified at 208 by the processing unit 118. The candidate acquisition condition shown in the acquisition condition window 318 corresponds to the scan prescription shown on the activity window 302. In connection with FIG. 3, the acquisition condition window 318 includes a noise index target 304 and a projected noise index 308, which may correspond to a calculated image quality based on the scan prescription. The noise index target 304 and the projected noise index 308 may correspond to the acquisition condition target and the candidate acquisition condition, respectively. The noise index target 304 may be received by the processing unit 118 from the user interface 160, as described at 202. The projected noise index 308 corresponds to a projected or estimated image quality calculated by the processing unit 118 based on or corresponding to the scan projection (e.g., as described at 208). Additionally or alternatively, the acquisition condition window 318 may also include a projected dosage 322 corresponding to the projected or estimated dosage calculated by the processing unit 118 based on the scan projection.

It should be noted various other embodiments may include additional or fewer interface components, differently sized interface components, and/or interface components having a different orientation or position relative to the interface components shown in FIG. 3.

At 214, the processing unit 118 determines whether confirmation of the scan prescription is received. The processing unit 118 may determine confirmation of the scan prescription based on activation of corresponding interface components (e.g., graphical icons 320, 324) shown in the display interface 300. For example, selection of the graphical icon 324 may correspond to confirmation of the scan prescription displayed within the activity window 302. In another example, selection of the graphical icon 320 may correspond to a request to the processor unit 118 to adjust the scan prescription.

Optionally, the processing unit 118 may determine confirmation of the scan prescription based on the difference or disparity between the acquisition condition target and the candidate acquisition condition of the scan prescription. For example, the processing unit 118 may compare the difference between the acquisition condition target and the candidate acquisition condition with a predetermined threshold. If the difference is under the predetermined threshold, the processing unit 118 may determine that the scan prescription is confirmed. Alternatively, if the difference is above the predetermined threshold, the processing unit 118 may determine that the scan prescription is not confirmed.

If the scan prescription is not confirmed, at 216, the processing unit 118 identifies an alternative scan prescription, such as a second scan prescription. The second scan prescription may include one or more alternative select scan settings relative to the scan prescription identified at 210. Additionally or alternatively, based on the one or more alternative select scan settings, the second scan prescription may have a different candidate acquisition condition compared to the scan prescription. Particularly, the second scan prescription may have a candidate acquisition condition more proximate to the acquisition condition target relative to the scan prescription. For example, the second scan prescription may have a higher image quality (e.g., noise index) relative to the scan prescription.

In various embodiments, the second scan prescription may correspond to a trade-off of the dose target and image quality of the candidate acquisition conditions with respect to the acquisition condition target. For example, a relationship may exist between the dose target and the image quality such that increasing the dose target may increase the image quality of the resultant medical image. Based on the relationship, the processing unit 118 may select and/or determine a technical trade-off or exchange between the image quality and dose target relative to the scan prescription identified in 210 to identify the second scan prescription. The technical trade-off may correspond to identifying a second scan prescription based on a portion of the scan attribute.

For example, the second scan prescription may correspond to a calculated candidate acquisition condition having an image quality or dose more proximate and/or closer to the acquisition condition target relative to the candidate acquisition condition of the scan prescription identified at 210. The improved (e.g., relative to the scan) image quality or dose with respect to the acquisition condition target may be a trade-off or in exchange for having the dose or image quality, respectively, being distant and/or further away from the acquisition condition target relative to the scan prescription identified at 210. Optionally, the processing unit 118 may identify additional scan prescriptions by iteratively adjusting the trade-off between the image quality or dose to have the image quality or dose be more proximate to the acquisition condition target with respect to a previously identified scan prescription.

The processing unit 118, based on the scan attribute of the CID, may identify the second scan prescription. Generally, the second scan prescription may relate to a tradeoff on characteristic(s) of the resultant medical image based from the scan attribute to achieve an acquisition condition more proximate to the acquisition candidate target. The processing unit 118 may select the second scan prescription based on a degree of freedom attribute of the scan attribute and/or secondary scan attribute generated from the CID, which corresponds to characteristic(s) of the resultant medical image that is not needed for the diagnostics or measurements based on the CID. For example, the processing unit 118 may select scan settings for the second scan prescription that reduce a presence and/or occurrence of characteristics of the resultant medical image that correspond to the degree of freedom attributes. The processing unit 118 may select one or more alternative select scan settings that may be contrary to and/or provides minimal value to the scan attribute relating to the degree of freedom attributes or secondary scan attribute relative to the scan prescription.

For example, the CID may correspond to an instrumented spine examination having primary scan attributes of high spatial resolution and an artifact suppression attribute, a secondary scan attribute of low contrast detectability (LCD), and degree of freedom attributes of high temporal resolution and material discrimination. The processing unit 118 may select alternative scan settings for selection of a second scan prescription from the plurality of scan settings of the profile database based on only the primary and secondary scan attributes. For example, the processing unit 118 may compare the scan attributes of the profile database with the primary and secondary scan attributes generated of the CID. When the processing unit 118 determines a match, the processing unit 118 may flag the corresponding scan settings and calculate associating candidate acquisition conditions. The processing unit 118 may identify one of the alternative select scan settings as the second scan prescription based on a relation between the candidate acquisition conditions and the acquisition condition target as similarly described at 210.

Figure 4:
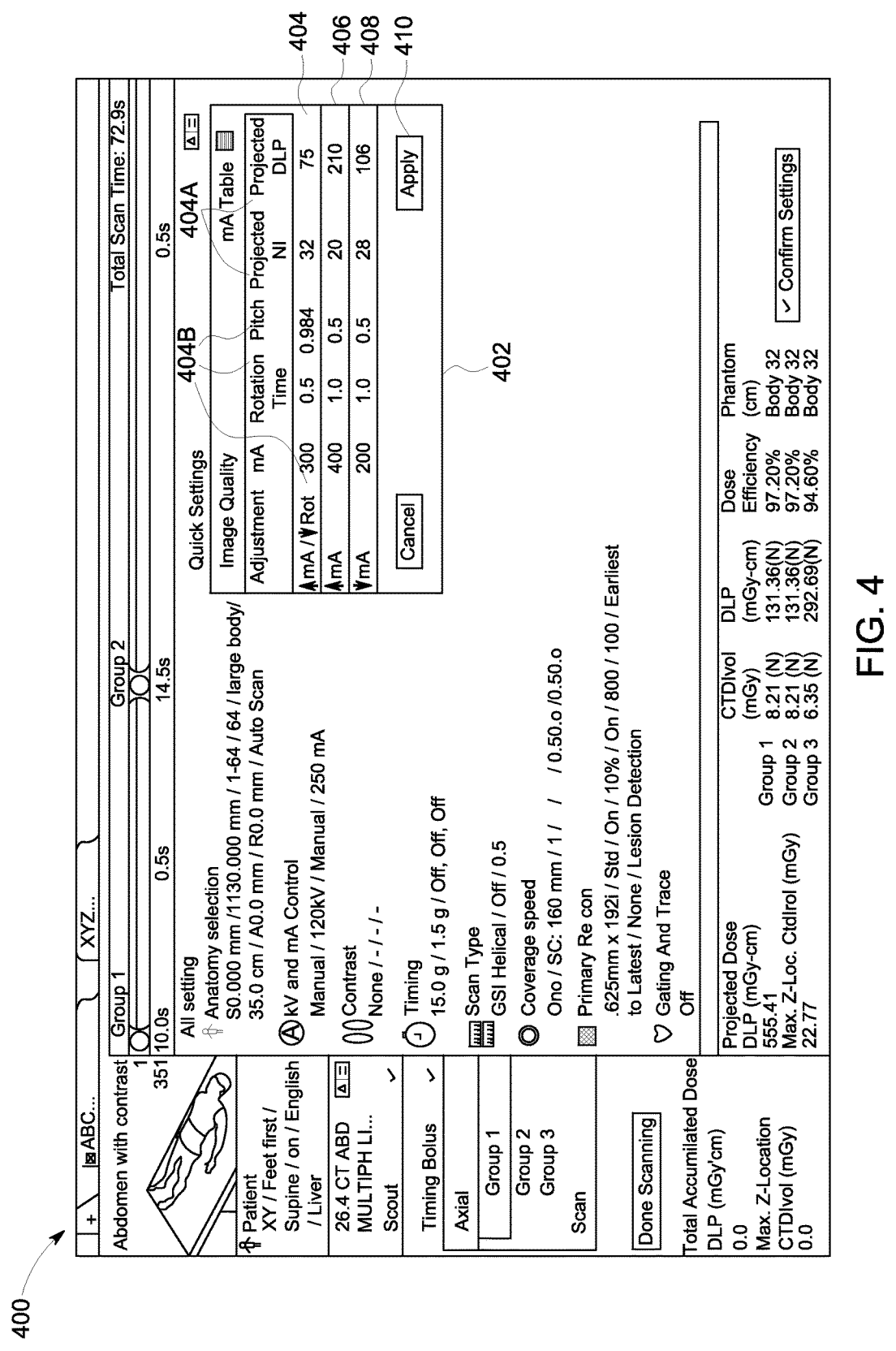

In connection with FIG. 4, an alternative scan prescription window 402 may display information regarding the second scan prescription identified by the processing unit 118. For example, the alternative scan prescription window 402 may include the candidate acquisition condition 404*a* (e.g., noise index, dosage) and the one or more alternative scan settings 404*b* of the second scan prescription along a user selectable row 404 determined by the processing unit 118.

FIG. 4 illustrates a display interface 400 shown on the display 162, which may include similar interface components as described in relation to the display interface 300 shown in FIG. 3. The alternative scan prescription window 402 may include additional scan prescriptions along user selectable rows 406-408 identified by the processing unit 118 as described herein, which may have additional scan settings and/or candidate acquisition conditions different than the scan prescription and the second scan prescription. The alternative scan prescription window 402 may also allow the user to select one of the alternative scan prescriptions (e.g., the second scan prescription, one of the additional scan prescriptions) by activating or selecting one of the corresponding user selectable rows 404-408. Optionally, the alternative scan prescription may be applied based on activation and/or selection of a graphical icon 410.

Additionally or alternatively, the processing unit 118 may determine additional scan prescriptions, such as the additional scan prescriptions 406-408 shown in FIG. 4, by iteratively omitting one of the degree of freedom attributes and/or secondary scan attributes after a scan prescription is identified. For example, the processing unit 118 may identify two, three, four, and/or more additional scan prescriptions.

Optionally, the processing unit 118 may display the one or more identified scan prescriptions (e.g., the scan prescription identified at 210, the second scan prescription identified at 216, additional scan prescriptions) with corresponding acquisitions conditions concurrently on a display interface (e.g., the display interface 300, the display interface 400) to allow the user to select and/or confirm one of the displayed scan prescriptions.

Returning to FIG. 2, if the scan prescription is confirmed, at 218, medical image data is acquired corresponding to the scan prescription. For example, the acquisition subsystem 142 may govern the rotation speed and position of the gantry 110, power and timing signals of the X-ray source 112, and position of the motorized table 122 during the scan based on the scan settings of the scan prescription. A group of X-ray attenuation measurements corresponding to the medical image data are measured at the detector array 114 corresponding to X-ray emissions from the X-ray source 112. The data acquisition system (DAS) 148 converts the projection data to digital signals for subsequent processing by the image reconstructor 150.

Figure 5:
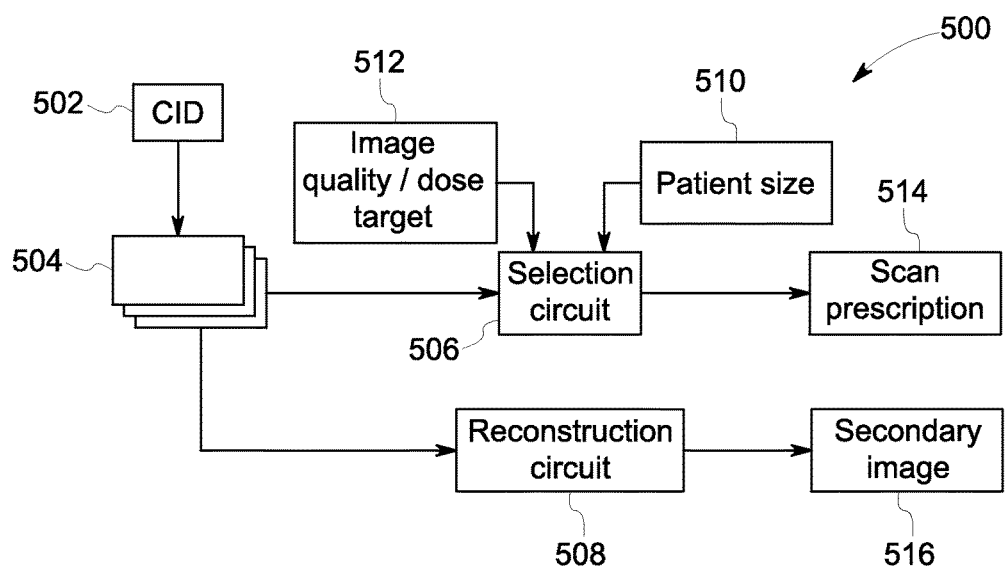
FIG. 5 illustrates a schematic process flow for guided selection of acquisition parameters in accordance with various embodiments.

FIG. 5 illustrates a schematic process flow 500 for guided selection of acquisition settings for imaging systems. It may be noted that the various blocks depicted in FIG. 5 may represent process steps in some embodiments and/or components or aspects configured to perform process steps in some embodiments (e.g., the processing unit 118). Generally, as seen in FIG. 5, a selection of acquisition parameters corresponding to a scan prescription are derived from a profile database based on a clinical identifier (CID), one or more patient characteristics, and an acquisition condition target (e.g., contrast dosage target, noise index). In various embodiments, certain blocks may be omitted, and/or additional process blocks may be added (see, e.g., FIG. 2).

For the embodiment depicted in FIG. 5, at block 502, a clinical identifier (CID) is received corresponding to a clinical context for the scan. The CID provides one or more scan attributes needed for a resultant medical image. The CID may be received from a user via a user interface (e.g., the user interface 160), received remotely from a patient database, and/or the like. The CID may include an anatomy of interest (e.g., organ of interest, region of interest) of the patient 123 and a clinical indication corresponding to the purpose or objective of the CT scan. The CID may be received by the processing unit 118 from the user interface 160.

In the illustrated embodiment, at block 504 select scan settings from a plurality of scan settings are selected (e.g., by the processing unit 118) based on the CID. In connection with FIG. 6, the CID may be mapped to a profile database to determine select scan settings which may generate a resultant medical image having the one or more scan attributes corresponding to the CID.

Figure 6:
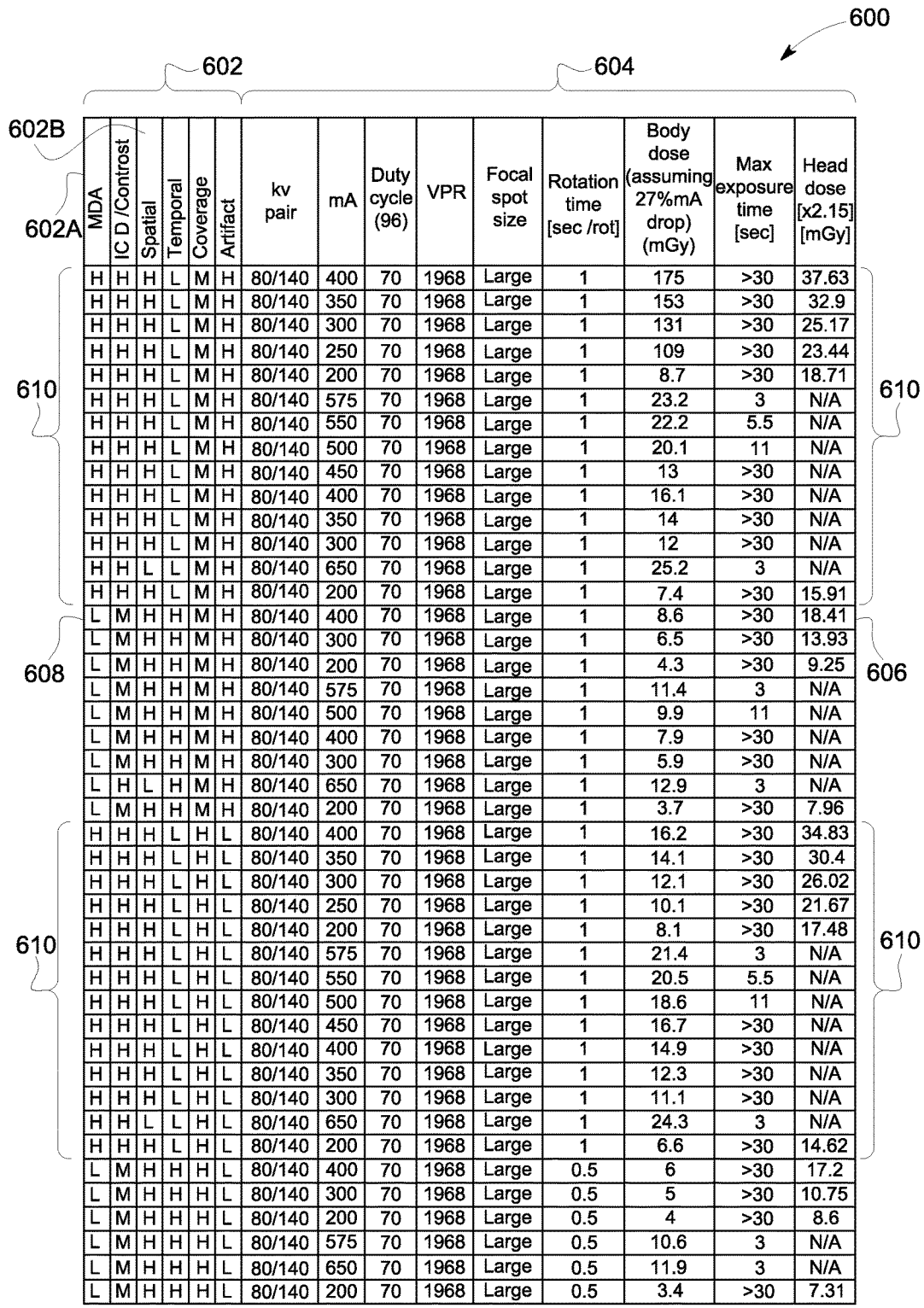
FIG. 6 illustrates a profile database in accordance with various embodiments.

FIG. 6 is an illustration of a profile database 600 in accordance with an embodiment. The profile database 600 includes a plurality of scan settings 604. The scan settings 604 may be constructed from priori information (e.g., patient population acquisition studies, pre-programmed rule sets) and/or generated from user inputs received by the user interface 160. The profile database includes a plurality of scan attributes 602, such as material discrimination accuracy (MDA) 602a and spatial resolution 602b. It should be noted that in various other embodiments the profile database 600 may include additional and/or alternative scan settings 604, scan attributes 602, corresponding values, and/or the like.

The scan attributes 602 may be assigned a value (e.g., such as high, medium, low, a percentage, a magnitude) corresponding to an amount and/or presence of an image characteristic and/or acquisition characteristic of the resultant medical image using the scan settings 604 linked and/or corresponding to the scan attributes 602. For example, at reference 608, the value 'L' may correspond to a low MDA 602a in the resultant medical image acquired with a scan prescription using the scan settings 604 on the row 606.

The scan attributes corresponding to the CID may be matched with the scan attributes 602 to select one or more select scan settings 604. For example, the CID may correspond to a kidney stone characterization having a primary scan attribute of a high MDA and a degree of freedom attribute of a high spatial and temporal resolution. The processing unit 118, corresponding to the operation at the block 504, may select scan settings 604 having scan attributes 602 with high MDA and high spatial resolution and temporal resolution. Optionally, a portion of the scan attributes (e.g., the degree of freedom attribute, the secondary scan attribute) may be ignored and/or disregarded if the select scan settings 604 could not be matched. For example, the scan attributes 602 listed in the scan profile 600 does not include scan settings 604 resulting in and/or corresponding to scan attributes 602 having a high MDA and high temporal resolution. When no match was found, the degree of freedom attribute may be ignored and/or disregarded to determine a match within the profile database. For example, the degree of freedom attributes of the CID corresponding to the kidney characterization of spatial resolution and temporal resolution may be ignored and/or disregarding for the selection of select scan settings 604. Based on the remaining scan attributes, e.g., the primary scan attributes, the processing unit 118 may select the scan settings 604 at rows 610 having a high MDA scan attribute as the selected scan settings 604.

Returning to FIG. 5, a selection circuit block 506 may identify one of the select scan settings 604 selected at the block 504 as a scan prescription 514 corresponding to the acquisition settings for the resultant medical image. The scan prescription 514 may be identified by the selection circuit block 506 from the select scan settings 604 based on a patient size 512 and an image quality and dose targets 510. The patient size 512 may be determined from a scout scan. The selection circuit block 506 may determine which of the select scan settings 604 may be affected by the patient size 512, such as reducing the scan attributes in a resultant medical image. The selection circuit block 506 may further calculate candidate image quality and corresponding doses associated with the select scan settings to determine which of the select scan settings may be proximate to and/or the same as the image quality and dose targets 510. The selection circuit block 506 may identify the select scan settings which may generate the resultant medical image having scan attributes and have acquisition conditions the same and/or more proximate to the targets 510.

A reconstruction circuit block 508 may select one or more reconstruction settings based on the scan attributes provided by the CID. The reconstruction settings may include select keV energy level(s), iterative reconstruction (e.g., adaptive statistical reconstruction), direct multi-planar reconstruction, algorithmic reconstruction (e.g., Native VUE®), and/or the like. The select one or more reconstruction settings may be in addition to reconstruction settings selected by the user via the user interface. For example, the reconstruction circuit block 508 may generate a secondary image 516, which may be reconstructed based on the select one or more reconstruction settings, in addition to the resultant medical image, which may be reconstructed based on reconstruction settings selected by the user. Optionally, the resultant medical image may include an image based CID, which may indicate or flag potential post-processing (e.g., measurements, diagnostics) that may be performed by one or more processors (e.g., the processing unit 118).

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "processing unit," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A computer implemented method comprising:
   utilizing one or more processors to perform the following operations:
   receiving a clinical identifier, an acquisition condition target, and one or more patient characteristics, wherein the acquisition condition target corresponds to an image quality target or a dosage target of a patient;
   generating a scan attribute based on the clinical identifier, wherein the scan attribute corresponds to a characteristic of a resultant medical image;
   determining select scan settings from a plurality of scan settings based on the scan attribute and the one or more patient characteristics;
   calculating candidate acquisition conditions associated with the select scan settings; and
   identifying one of the select scan settings as a scan prescription based on a relation between the candidate acquisition conditions and the acquisition condition target.

2. The method of claim 1, further comprising identifying a second scan prescription based on at least one of a degree of freedom attribute and a second scan attribute.

3. The method of claim 1, further comprising identifying a second scan prescription based on a portion of the scan attribute, wherein the scan attribute includes a primary scan attribute and at least one of a second scan attribute and a degree of freedom attribute.

4. The method of claim 3, wherein the second scan prescription is associated with a second candidate acquisition condition that is more proximate to the acquisition condition target relative to the candidate acquisition condition of the scan prescription.

5. The method of claim 1, further comprising:
selecting a reconstruction setting based on the scan attribute; and
generating the resultant medical image based on the reconstruction settings.

6. The method of claim 1, further comprising displaying on a display the scan prescription and a corresponding acquisition condition, wherein the corresponding acquisition condition includes a calculated image quality.

7. The method of claim 1, wherein the clinical identifier includes an anatomy of interest and a clinical scan identification.

8. The method of claim 1, wherein the scan attribute includes at least one of a temporal resolution, a material discrimination accuracy, a contrast to noise ratio, a coverage size, spatial resolution, a low contrast detectability, minimal coverage time, and an artifact suppression attribute.

9. A medical imaging system comprising:
an acquisition unit comprising one or more processors and a computed tomography (CT) detector configured to collect medical imaging data based on a scan prescription; and
a processing unit comprising one or more processors operably coupled to the acquisition unit, the processing unit configured to:
receive a clinical identifier, an acquisition condition target, and one or more patient characteristics, wherein the acquisition condition target corresponds to an image quality target or a dosage target of a patient;
generate a scan attribute based on the clinical identifier, wherein the scan attribute corresponds to a characteristic of a resultant medical image;
determine select scan settings from the plurality of scan settings based on the scan attribute and the one or more patient characteristics;
calculate candidate acquisition conditions associated with the select scan settings; and
identify one of the select scan settings as a scan prescription based on a relation between the candidate acquisition conditions and the acquisition condition target.

10. The medical imaging system of claim 9, wherein the processing unit is further configured to select a second scan prescription based on a degree of freedom attribute and a second scan attribute.

11. The medical imaging system of claim 10, wherein the second scan prescription is based on a trade-off between an image quality and a dose with respect to the acquisition condition target.

12. The medical imaging system of claim 9, further comprising a display configured to display the scan prescription and a corresponding acquisition condition, wherein the corresponding acquisition condition includes an image quality.

13. The medical imaging system of claim 9, wherein the clinical identifier includes an anatomy of interest and a clinical scan identification.

14. The medical imaging system of claim 9, wherein the scan attribute includes at least one of a temporal resolution, a material discrimination accuracy, a contrast to noise ratio, a coverage size, a spatial resolution, and an artifact suppression attribute.

15. A tangible and non-transitory computer readable medium comprising one or more computer software modules configured to direct one or more processors to:
receive a clinical identifier, an acquisition condition target, and one or more patient characteristics, wherein the acquisition condition target corresponds to an image quality target or a dosage target of a patient;
generate a scan attribute based on the clinical identifier, wherein the scan attribute corresponds to a characteristic of a resultant medical image;
determine select scan settings from the plurality of scan settings based on the scan attribute and the one or more patient characteristics;
calculate candidate acquisition conditions associated with the select scan settings; and
identify one of the select scan settings as a scan prescription based on a relation between the candidate acquisition conditions and the acquisition condition target.

16. The tangible and non-transitory computer readable medium of claim 15, wherein the one or more computer software modules are further configured to direct the one or more processors to select a second scan prescription based on at least one of a degree of freedom attribute and a second scan attribute.

17. The tangible and non-transitory computer readable medium of claim 16, wherein the second scan prescription is based on a trade-off between an image quality and a dose with respect to the acquisition condition target.

18. The tangible and non-transitory computer readable medium of claim 15, wherein the one or more computer software modules are further configured to direct the one or more processors to display the scan prescription and a corresponding acquisition condition, wherein the corresponding acquisition condition includes an image quality.

19. The tangible and non-transitory computer readable medium of claim 15, wherein the clinical identifier includes an anatomy of interest and a clinical scan identification.

20. The tangible and non-transitory computer readable medium of claim 15, wherein the scan attribute includes at least one of a temporal resolution, a material discrimination accuracy, a contrast to noise ratio, a coverage size, a spatial resolution, and an artifact suppression attribute.

* * * * *